United States Patent [19]

Mummery et al.

[11] 4,005,606
[45] Feb. 1, 1977

[54] SUBMERSIBLE LOAD CELL FOR MEASURING GAS BUOYANCY

[75] Inventors: Herbert L. Mummery, Kaneohe; Robert T. Hoffmann, Kailua, both of Hawaii

[73] Assignee: The United States of America as represented by the Secretary of the Navy, Washington, D.C.

[22] Filed: Sept. 29, 1975

[21] Appl. No.: 617,912

[52] U.S. Cl. .................................................. 73/438
[51] Int. Cl.[2] ........................................... G01N 9/12
[58] Field of Search ............... 73/438, 32 R, 170 A, 73/398 AR, 141 R

[56] References Cited
UNITED STATES PATENTS

| | | | |
|---|---|---|---|
| 1,395,653 | 11/1921 | Nernst | 73/398 AR |
| 3,193,853 | 7/1965 | Alexander | 73/170 A |
| 3,293,676 | 12/1966 | Link | 73/170 A |

OTHER PUBLICATIONS

Pochapsky, I.S.A. Journal, "Exploring Subsurface Waves with Neutrally Buoyant Floats", vol. 8, No. 10, Oct., 1961, pp. 34–37.

Primary Examiner—Richard C. Queisser
Assistant Examiner—Stephen A. Kreitman
Attorney, Agent, or Firm—Richard S. Sciascia; Ervin F. Johnston

[57] ABSTRACT

A submersible load cell for measuring gas buoyancy which includes a shell which has an open bottom so that gas can be introduced to make the shell positively buoyant. A framework may be provided for supporting the shell for vertical movement so that a change in buoyancy results in the shell exerting a corresponding upward force. At least one hydraulic actuator is mounted between the framework and the shell for registering a pressure which corresponds to the degree of upward force or positive buoyancy of the shell. An indicator device can be connected to the hydraulic actuator for indicating the change in buoyancy of the shell as gas is introduced therein.

10 Claims, 5 Drawing Figures

(LOAD CELL)

SUBMERSIBLE LOAD CELL FOR MEASURING GAS BUOYANCY

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The U.S. Navy has performed considerable research in manned and unmanned deep submersibles for salvage, reconnaissance, and surveillance work. One of the plausible methods for changing the buoyancy of these submersibles has been the utilization of various generated gases. One gas which has shown promise is hydrazine which is stored in liquid form and converted to a gas over a catalyst bed for increasing the buoyancy of the submersible.

In the utilization of a specific gas as well as the design of the submersible it has become necessary to ascertain the degree of buoyancy achieved from various gas sources at various ocean depths. The most practical way of accomplishing such a test is to perform it at the desired ocean depth. A gas generation device, such as a hydrazine generator, generates the gas which is transferred to a load cell. The load cell is utilized for indicating the degree of buoyancy achieved at the specified depth.

The prior art offers very little in the way of a load cell which can be utilized at an ocean depth for determining the buoyancy achieved from generated gases. One method investigated was a collapsible bag for containing the buoyancy gases wherein the bag is connected to a spring system for scribing the buoyancy increase on a piece of plexiglass. This combination did not have adequate sensitivity due to the friction effects of the springs and the scribe. It was found that friction is the biggest problem to overcome in providing an adequate buoyancy indicator. Subsequently, the scribe was replaced with a linear potentiometer, and again the friction of the springs prevented accurate measurement of the small changes in the buoyancy. Commercial load measuring devices include a "fish scale" type which has no capacity for direct recording of the measurement. Commercial hydraulic units are designed to weigh loads hanging from them in a homogenous gravity field. These devices are generally unsuitable for ocean measurements due to their high weight coupled with the fact that gravity acts downward on the cell components, which are generally heavy, while the buoyancy measurement is directed upward. Many of the commercial devices do not lend themselves to salt water immersion.

SUMMARY OF THE INVENTION

The present invention provides a submersible load cell which is capable of accurately measuring gas buoyancy. This has been accomplished by providing a shell which has an open bottom so that gas can be introduced to make the shell positively buoyant. A framework may support the shell for vertical movement so that a change in buoyancy results in the shell exerting a corresponding upward force. At least one hydraulic actuator is mounted between the supporting framework and the shell for registering a pressure which corresponds to the degree of upward force or positive buoyancy of the shell. An indicating device is connected to the hydraulic actuator for indicating the change in buoyancy of the shell as a gas is introduced therein. With such an arrangement changes in buoyancy can be ascertained at various depths in the ocean for determining the efficiency of various gases and their corresponding generators.

DESCRIPTION OF THE PREFERRED EMBODIMENT

Figure 1:
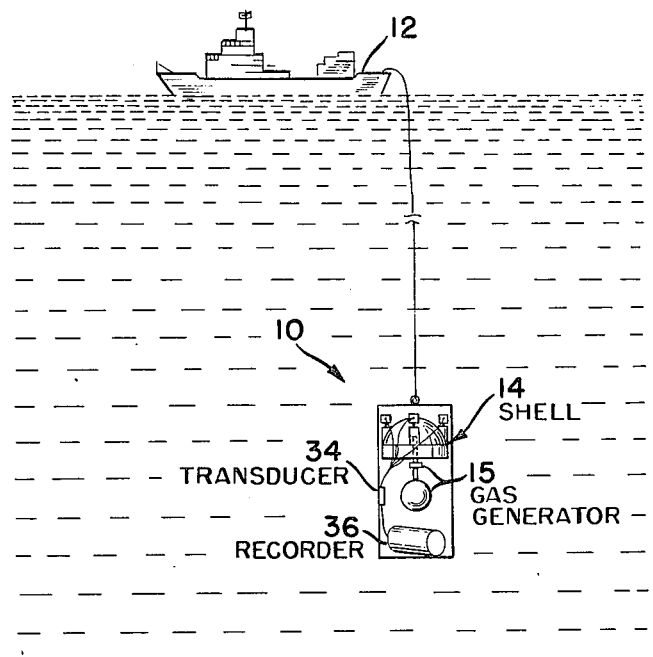
FIG. 1 is an ocean elevation schematic view illustrating a suspended apparatus including the load cell for recording changes in buoyancy due to generated gas.

Referring now to the drawings wherein like reference numerals designate like or similar parts throughout the several views, there is illustrated in FIG. 1 a submersible apparatus 10 which is suspended at a depth in the ocean by a surface vessel 12. The apparatus 10 includes a load cell 14 which is capable of measuring gas buoyancy at the ocean depth. Gas is supplied to the load cell 14 by a gas generator 15 which may include a pressurized liquid hydrazine supply tank 60 and a catalyst bed 62 for converting the liquid hydrazine to gas.

Figure 2:
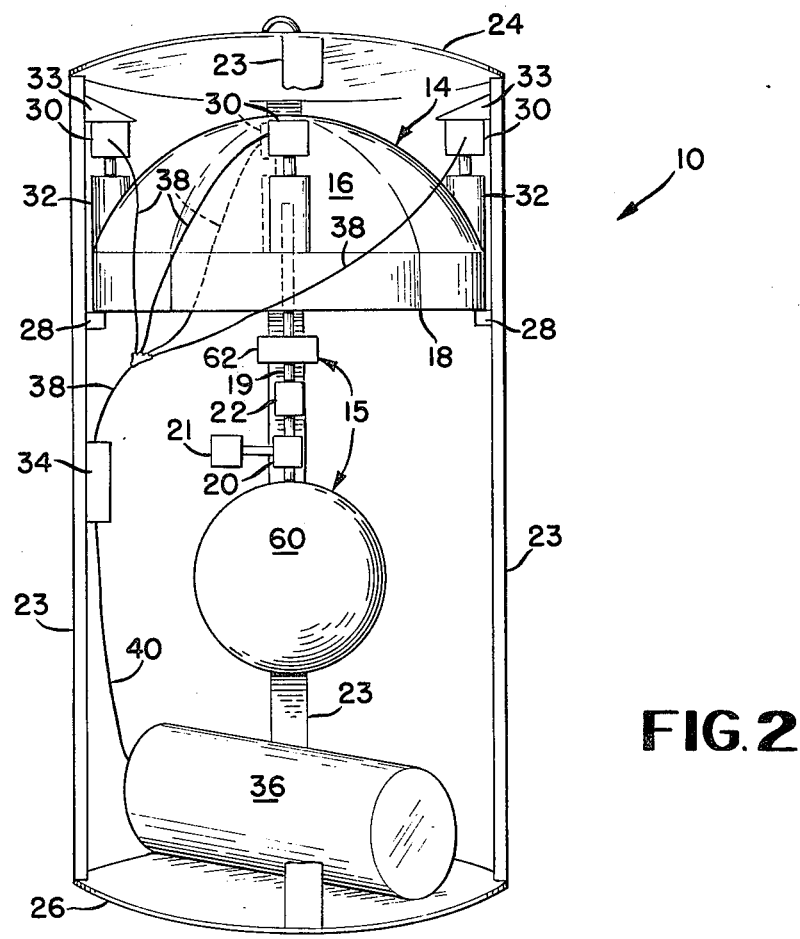
FIG. 2 is an isometric schematic view of the suspensible apparatus including the load cell.
Figure 3:
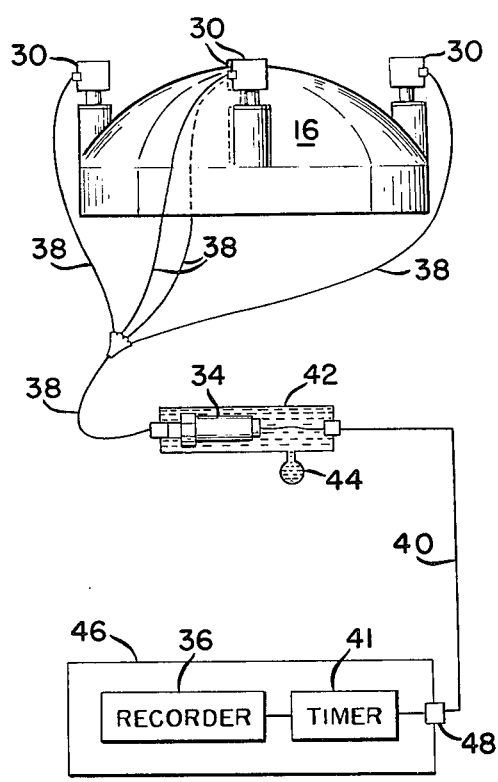
FIG. 3 is a schematic illustration of the load cell.

As illustrated in FIGS. 2 and 3 the load cell 14 includes a shell 16 which has an open bottom 18 so that gas can be introduced from the gas generator 15 by any suitable means such as a conduit 19 which extends into the shell 16. The shell 16 may have a hemispherical portion as illustrated in FIGS. 2 and 3. A valve 20 and a timer 21 may be interconnected in the conduit 19 for introducing the gas into the shell 16 after the apparatus 10 has descended to the desired ocean depth. A flow meter 22 interconnected in the conduit 19 may be utilized for indicating the total volume of liquid fuel used to generate the gas fed to the shell 16.

Means are provided for supporting the shell 16 for vertical movement so that a change in buoyancy results in the shell exerting a corresponding upward force. The support means may include a framework which has four upstanding columns 23 which are joined in a spaced apart relationship by top and bottom plates 24 and 26. The columns 23 receive the hemispherical shell 16 in a loose manner, and are provided with stops 28 to limit the downward movement of the shell within the framework. With this arrangement it can be readily visualized that introduction of gas into the hemispherical shell 16 will cause the shell to increase its buoyancy and ultimately exert an upward force.

At least one hydraulic actuator 30 is mounted between the framework and the shell 16 for registering a pressure which corresponds to the degree of upward force or positive buoyancy of the shell. Preferably four such hydraulic actuators are employed. Each hydraulic actuator 30 is simply a piston and cylinder combination which converts the upward buoyancy force of the shell 16 to liquid pressure. Each hydraulic actuator 30 may be mounted on built-up foot portions 32 on the shell 16 and may apply their forces against upper stop members 33 on the columns 23.

Means are connected to the hydraulic actuators 30 for indicating the change in buoyancy of the shell 16 as gas is introduced therein by the gas generator 15. The indicator means may include a pressure transducer 34 and a recorder 36. Hydraulic lines 38 may connect the hydraulic actuators 30 to the liquid input of the transducer 34, and an electrical lead 40 may connect the electrical output of the transducer 34 to the input of the recorder 36. The recorder 36 may include its own power source and may be of the chart type with a trace indication for showing the change in buoyancy. The recorder may be started by a timer 41 after the apparatus 10 has descended to the test depth.

Figure 5:
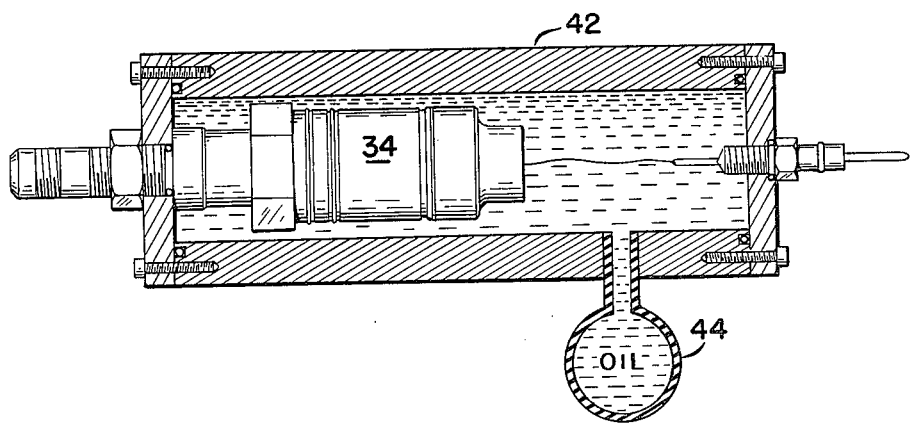
FIG. 5 is a side view partially in cross section of a pressure transducer for the load cell.

As illustrated in FIGS. 3 and 5 the pressure transducer 34 may be mounted in a sealed housing 42, and this housing may be filled with an electrically resistive liquid, such as silicone oil. The housing 42 may be pressure compensated by an accumulator 44. With this arrangement the transducer 34 will be subjected to the same ambient pressure as the shell 16 and hydraulic actuators 30 so as to be more responsive to the pressure indications from the hydraulic actuators 30. The recorder 36 is preferably mounted in a pressure casing 46 so that the recorder 36 is maintained at surface pressure during the operation. Penetrators 48 may be provided in the hydraulic actuators 30, the housing 42, and the casing 46 for pressure sealing the hydraulic lines 38 and the electrical lead 40 in these respective components.

Figure 4:
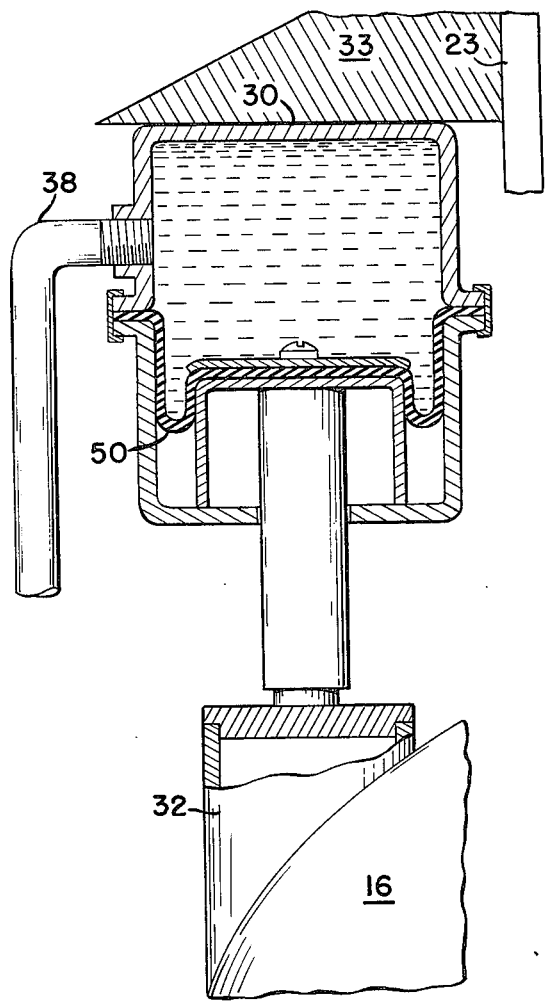
FIG. 4 is a cross sectional view of one of the hydraulic actuators of the load cell.

It is important that the load cell 14 operate as friction free as possible. As illustrated in FIG. 4, this has been accomplished by utilizing a piston and cylinder actuator which utilizes a Bellofram rolling diaphragm 50. Further, the columns 23 are spaced apart slightly greater than the cross dimension of the shell 16 so that there is no friction between the shell and the interior surfaces of the columns 23. With this arrangement, the upward force of the shell 16 due to buoyancy is substantially entirely reflected in corresponding pressures in the actuators 30.

After calibration of the load cell 14 the trace displacement on the recorder 36 as a function of time can be converted to upward buoyancy force exerted by the shell 16 as gas is introduced therein from the generator 15. The load cell may be calibrated by a two-step procedure. First, the shell 16 is inverted and filled with water while the pressure of the actuators 30 is recorded. This will provide an actuator pressure versus water volume profile which in turn can be utilized to provide an actuator pressure versus buoyancy force profile since the water volume can be easily converted to force. The next step in the calibration procedure includes pressurizing the actuators 30 and noting the trace displacement on the recorder 36 versus applied pressure. This pressure is then converted to buoyancy force from the first step of the procedure in order to provide an indication of change in buoyancy versus trace displacement.

OPERATION OF THE INVENTION

The load cell 14 is capable of indicating the efficiency of generated gas for providing buoyancy at various ocean depths. This is accomplished by the surface vessel 12 deploying the apparatus 10 to the test depth, after which gas is generated by the gas generator 15 and disseminated into the shell 16. The flow meter 22 will indicate the total volume of fuel dispensed. As the gas is introduced into the shell 16, water is displaced therefrom and and upward buoyancy force is exerted. When this force exceeds the weight of the shell 16 in water, an upward force will be applied to the actuators 30 which will apply a liquid pressure to the transducer 34. The transducer 34 converts the liquid pressure to an electrical signal which is fed to the recorder 36 which will in turn record a change in buoyancy. The volume of fuel dispensed, as indicated by the flow meter 22, and the change in buoyancy will enable a determination of the efficiency of the generated gas and the gas generator 15. This information then lends to the selection of the proper gas, gas generator, and design of the submersible which is to utilize the gas.

Obviously, many modifications and variations of the present invention are possible in the light of the above teachings, and, it is therefore understood that within the scope of the disclosed inventive concept, the invention may be practiced otherwise than specifically described.

What is claimed is:

1. A submersible load cell for measuring gas buoyancy comprising:
   a rigid shell which has an open bottom so that gas can be introduced therein to make the shell positively buoyant;
   means supporting the shell for vertical movement so that a change in buoyancy results in the shell exerting a corresponding upward force;
   at least one hydraulic actuator mounted between the support means and the shell for registering a pressure which corresponds to the degree of upward force or positive buoyancy of said shell; and
   means connected to the hydraulic actuator for indicating the change in buoyancy of the shell as gas is introduced therein.

2. A load cell as claimed in claim 1 including:
   the indicator means being a pressure transducer and a recorder; and
   the pressure transducer being connected to the hydraulic actuator and the recorder being connected to the pressure transducer.

3. A load cell as claimed in claim 2 including:
   the pressure transducer being mounted in a housing;
   said housing being filled with an electrically resistive liquid; and
   means connected to the housing for pressure compensating the housing.

4. A load cell as claimed in claim 3 including:
   the recorder being mounted in a pressure casing.

5. An apparatus as claimed in claim 1 including:
   said hydraulic actuator being of the Bellofram rolling diaphragm type.

6. a load cell as claimed in claim 5 including:
   said shell having a top hemispherical portion;
   a plurality of hydraulic actuators of the Bellofram rolling diaphragm type mounted on the shell in a spaced relationship and engageable with the support means; and
   said pressure transducer being connected to all of the hydraulic actuators.

7. A load cell as claimed in claim 6 including:
   the indicator means being a pressure transducer and a recorder; and
   the pressure transducer being connected to the hydraulic actuator and the recorder being connected to the pressure transducer;
   the pressure transducer being mounted in a housing;

said housing being filled with an electrically resistive liquid; and means connected to the housing for pressure compensating the housing; and the recorder being mounted in a pressure casing.

8. A submersible load cell for measuring gas buoyancy comprising:

a rigid shell which has an open bottom so that gas can be introduced therein to make the shell positively buoyant;

framework means;

said shell being slidably mounted to the framework means for reciprocable vertical movement;

said framework means being open therealong so that the shell is subjected to ambient pressure from all sides;

the shell being mounted in the framework with its open bottom directed downwardly so that gas can be introduced into the shell through its open bottom;

the introduction of gas into the shell causing the shell to exert an upward force which corresponds to its positive buoyancy;

at least one hydraulic actuator mounted between the support means and the shell for registering a pressure which corresponds to the degree of upward force or positive buoyancy of said shell; and means connected to the hydraulic actuator for indicating the change of buoyancy of the shell as gas is introduced therein.

9. A load cell as claimed in claim 8 including:

means mounted to the framework means for introducing gas into the shell through said open bottom.

10. A load cell as claimed in claim 9 including:

means mounted to the framework means and connected to the gas introducing means for generating gas from a liquid fuel; and means connected to the gas generation means for measuring and indicating the total volume of liquid fuel utilized to generate gas which has been fed to said shell;

whereby the efficiency of the liquid fuel utilized in generating gas at some water depth can be ascertained by comparing volume of liquid fuel utilized with the upward buoyancy force attained.

* * * * *

UNITED STATES PATENT OFFICE
CERTIFICATE OF CORRECTION

Patent No. 4,005,606     Dated February 1, 1977

Inventor(s)     Herbert L. Mummery et al.

It is certified that error appears in the above-identified patent and that said Letters Patent are hereby corrected as shown below:

On the cover sheet co-inventor's name "Robert T. Hoffmann" should read -- Robert T. Hoffman --.

Signed and Sealed this

Seventh Day of February 1978

[SEAL]

Attest:

RUTH C. MASON
Attesting Officer

LUTRELLE F. PARKER
Acting Commissioner of Patents and Trademarks